US00PP10399P

United States Patent [19]

Trees

[11] Patent Number: Plant 10,399

[45] Date of Patent: May 12, 1998

[54] GERANIUM PLANT NAMED 'BFP-1328 RED'

[75] Inventor: Scott C. Trees, Arroyo Grande, Calif.

[73] Assignee: Ball Horticultural Company, West Chicago, Ill.

[21] Appl. No.: 701,151

[22] Filed: Aug. 21, 1996

[51] Int. Cl.[6] ..... A01H 5/00

[52] U.S. Cl. ..... Plt./87.12

[58] Field of Search ..... Plt./87.12

[56] References Cited

U.S. PATENT DOCUMENTS

| | | | |
|---|---|---|---|
| P.P. 9,489 | 3/1996 | Endisch | Plt./87.12 |
| P.P. 9,496 | 4/1996 | Endisch | Plt./87.12 |
| P.P. 9,535 | 4/1996 | Trees | Plt./87.12 |
| P.P. 9,544 | 5/1996 | Trees | Plt./87.12 |
| P.P. 9,551 | 5/1996 | Trees | Plt./87.12 |
| P.P. 9,571 | 6/1996 | Endisch | Plt./87.12 |

*Primary Examiner*—Howard J. Locker
*Assistant Examiner*—Kent L. Bell
*Attorney, Agent, or Firm*—Burns, Doane, Swecker & Mathis, L.L.P.

[57] ABSTRACT

The new and distinct *Pelargonium×hortorum* cultivar named 'BFP-1328 Red' is provided.This new Zonal Geranium was the result of a controlled breeding program wherein a plant designated 6583-52 (non-patented in the United States) was crossed. More specifically, 6583-52 served as both the female parent and the male parent. The new cultivar forms attractive velvety semi-double intense red florets. The medium green foliage with zonation is well retained during shipment. The growth habit is vigorous self-branching and does not require the use of a growth regulator.

1 Drawing Sheet

SUMMARY OF THE INVENTION

The present invention comprises a new and distinct Geranium cultivar, botanically known as *Pelargonium×hortorum* Bailey, and hereinafter is referred to by the cultivar name 'BFP-1328 Red'.

The new cultivar is a product of a planned breeding program which had the objective of the creation of a Geranium cultivar that exhibits uniform flowers, medium green foliage, a vigorous self-branching growth habit that requires no growth regulator, a propensity for rapid rooting, and stable foliage coloration during shipment.

The breeding program that resulted in the production of the new cultivar of the present invention was carried out in a controlled environment during 1993 at Arroyo Grande, Calif., U.S.A. A plant designated 6583-52 (non-patented in the United States) served as both the female parent and the male parent and exhibited semi-double dark red florets and dark green foliage. The parentage of the new 'BFP-1328 Red' cultivar can be summarized as follows:

6583-52×6583-52.

'BFP-1328 Red' was discovered and selected during 1993 as a highly distinctive flowering plant from among the progeny of the stated cross at Arroyo Grande, Calif., U.S.A. This plant was initially designated BFP-1328.

It was found that the new cultivar of the present invention:

(a) exhibits attractive semi-double velvety intense red florets,
(b) forms attractive medium green foliage with zonation, and
(c) exhibits a vigorous self-branching growth habit in the absence of a growth regulator.

After senescence the flowers abscise and drop. To date, observations of the new 'BFP-1328 Red' cultivar have not demonstrated resistance to Botrytis or any other specific disease.

The first act of asexual reproduction of the 'BFP-1328 Red' cultivar was accomplished when vegetative cuttings were taken from the initial selection in a controlled environment at Arroyo Grande, Calif., U.S.A., by a technician working under the direction and supervision of the originator of the new cultivar. Horitcultural examination of plants resulting from such asexual propagation during 1994 has demonstrated that the combination of unique characteristics as herein described for the 'BFP-1328 Red' cultivar is fixed and is retained through successive generations of such asexual reproduction.

The new 'BFP-1328 Red' cultivar has not been observed under all possible environmental conditions. Accordingly, the described phenotype may vary somewhat with variations in the environment, such as temperature, light intensity, and day length.

Of the many commercial cultivars, the 'BFP-420 Bright Red' cultivar (U.S. Plant Pat. No. 9,219) is considered to be the most similar to the new cultivar of the present invention. When the new cultivar of the present invention is compared to the 'BFP-420 Bright Red' cultivar, it is found that the 'BFP-1328 Red' cultivar exhibits larger umbels (e.g., approximately 9 to 11 cm. vs. approximately 8.7 to 9 cm.), longer pedicels (e.g., approximately 3.2 to 4 cm. vs. approximately 2.6 to 2.9 cm.), larger florets (e.g., approximately 4.4 to 5.2 cm. vs. approximately 4 to 4.5 cm.), fewer florets per umbel (e.g., approximately 21 to 27 vs. approximately 39 to 41), a less vigorous growth habit (e.g., a plant height of approximately 18 to 22 cm. vs. approximately 28 to 29 cm.), and larger leaves.

The internode length is less and the blossom coloration of the new 'BFP-1328 Red' cultivar is different, than such characteristics of each of the cultivars discussed hereafter.

When compared to the 'BFP-788 Bright Scarlet' cultivar (U.S. Plant Pat. No. 9,551), it is found that 'BFP-788 Bright Scarlet' commonly forms larger umbels (e.g., approximately 10 to 12 cm.×7 to 10 cm. vs. approximately 9 to 11 cm.×6 to 7 cm.). Also, the peduncles of 'BFP-788 Bright Scarlet' tend to be longer (e.g., approximately 16 to 21 cm. vs. approximately 13 to 14.5 cm.), and the leaves are not zoned.

When compared to the 'BFP-838 Dark Red' cultivar (U.S. Plant Pat. No. 9,544), it is found that the 'BFP-838 Dark Red' cultivar has a significantly more vigorous growth habit (e.g., a height of approximately 24 to 30 cm. vs. a height of approximately 18 to 22 cm.).

When compared to the 'BFP-901 Bright Red' cultivar (U.S. Plant Pat. No. 9,535), it is found that the 'BFP-901 Bright Red' cultivar has a significantly more vigorous growth habit (e.g., a height of approximately 26 to 32 cm. vs. a height of approximately 18 to 22 cm.).

When compared to the 'Rena' cultivar (U.S. Plant Pat. No. 9,571), it is found that the 'Rena' cultivar commonly forms shorter umbels (approximately 5.4 to 5.6 cm. vs. approximately 6 to 7 cm.), longer peduncles (e.g., approximately 16 to 17 cm. vs. approximately 13 to 14.5 cm.), and more florets per umbel (e.g., approximately 35 vs. approximately 21 to 27).

When compared to the 'Faro' cultivar (U.S. Plant Pat. No. 9,489), it is found that the 'Faro' cultivar commonly forms more florets per umbel (e.g., approximately 38 approximately 21 to 27).

When compared to the 'Morella' cultivar (U.S. Plant Pat. No. 9,496), it is found that the 'Morella' cultivar commonly exhibits shorter umbels (e.g., approximately 4.6 to 4.8 cm. vs. approximately 6 to 7 cm.), and more florets per umbel (e.g., approximately 38 vs. approximately 21 to 27).

The new cultivar of the present invention is being marketed under the Designer trademark.

BRIEF DESCRIPTION OF THE PHOTOGRAPH

The accompanying photograph shows the new 'BFP-1328 Red' cultivar with colors being as nearly true as it is reasonably possible to make the same in a color illustration of this character. The plant was being grown in a greenhouse at West Chicago, Ill., U.S.A. The general appearance of the overall plant including the flower and foliage characteristics is illustrated.

DETAILED DESCRIPTION

The following observations, measurements and comparisons describe plants grown in greenhouses located at West Chicago, Ill., U.S.A., under conditions which approximate those generally used in commercial practice. In the following description, color references are made to the R.H.S. Colour Chart of The Royal Horticultural Society, London, England. The color values were determined on September 22nd, under natural light conditions of 200 footcandles.

Classification:

*Botanical.*—*Pelargonium×hortorum* Bailey, cv. 'BFP-1328 Red'.

*Commercial.*—Zonal Geranium.

Inflorescence

A. Umbel:

*Average diameter.*—Approximately 9 to 11 cm. compared to approximately 8.7 to 9 cm. for the 'BFP-420 Bright Red' cultivar.

*Average depth.*—Approximately 6 to 7 cm. compared to approximately 6 to 6.3 cm. for the 'BFP-420 Bright Red' cultivar.

*Peduncle length.*—Approximately 13 to 14.5 cm. compared to approximately 14 to 17 cm. for the 'BFP-420 Bright Red' cultivar.

*Pedicel length.*—Approximately 3.2 to 4 cm. compared to approximately 2.6 to 2.9 cm. for the 'BFP-420 Bright Red' cultivar.

*Number of umbels/plant.*—When grown in a 10 cm. pot at 9 weeks after the sticking of a rooted cutting, there commonly are approximately 4 to 5 umbels per plant. The 'BFP-420 Bright Red' cultivar also commonly forms approximately 3 to 5 umbels per plant.

*Number of florets/umbel.*—When grown in 10 cm. pots at 9 weeks, approximately 21 to 27 florets per umbel commonly are formed. This compares to approximately 39 to 41 florets per umbel for the 'BFP-420 Bright Red' cultivar under the same growing conditions.

B. Corolla:

*Buds.*—Round in configuration, bright red, Red Group 43A in coloration, and approximately 3 to 4 mm. in diameter.

*Pedicels.*—Commonly approximately 3.2 to 4 cm. in length.

*Average Diameter.*—Approximately 4.4 to 5.2 cm. compared to approximately 4 to 4.5 cm. for the 'BFP-420 Bright Red' cultivar.

*Form.*—Both the 'BFP-1328 Red' cultivar and the 'BFP-420 Bright Red' cultivar are semi-double with petaloids.

*Petals.*—Spatulate shaped, velvety, and smooth. Commonly approximately 5 to 9 petals are present per floret.

*Number of petaloids.*—The 'BFP-1328 Red' cultivar commonly possesses approximately 3 to 6 petaloids per floret. This can be compared to approximately 2 to 4 petaloids per plant for the 'BFP-420 Bright Red' cultivar.

*Color.*—General tonality from a distance of three meters: Bright red. Adaxial: Red Group 45B. This compares to Red Group 44A for the 'BFP-420 Bright Red' cultivar. Abaxial: Red Group 44B. This compares to Red Group 43B for the 'BFP-420 Bright Red' cultivar.

C. Reproductive organs;

*Androecium.*—The anthers are commonly approximately 2.5 mm. in length. The pollen color is Orange Group 28A for both the 'BFP-1328 Red' cultivar and the 'BFP-420 Bright Red' cultivar. The filaments are approximately 6 to 8 mm. in length.

*Gynoecium.*—The pistil length commonly is approximately 11 mm. There is a single stigma which commonly has a length of approximately 6 mm. which commonly branches into 5 parts, and the style length is approximately 3 mm.

*Fertility.*—Commonly does not produce fruits in the absence of mechanical fertilization.

D. Spring flowering response period: Approximately 6 to 7 weeks from rooted cuttings under standard greenhouse conditions.

E. Outdoor flower production: Freely flowering under outdoor growing conditions with substantially continous blooming.

F. Durability: Ships well.

Plant

A. Foliage: Medium green with zonation. The leaves are thin and puberulent.

*Form.*—Reniform, with a cordate base.

*Margin.*—Bi-crenate.

*Color.*—Adaxial: Green Group 143A at the center approximately one-third of the leaf and Green Group 143B at the remainder. This compares to Yellow-Green Group 146A for the 'BFP-420 Bright Red' cultivar. Abaxial: Green Group 143B. This compares to Yellow-Green Group 147B for the 'BFP-420 Bright Red' cultivar.

*Size.*—Approximately 9.2 to 10.4 cm in width at the widest point and approximately 7.9 to 9.3 cm. in length. This compares to approximately 8.6 to 9.2 cm. in width at the widest point and approximately 7.4 to 7.5 cm in length for the 'BFP-420 Bright Red' cultivar.

B. General appearance and form:

*Internode length.*—Commonly varies from approximately 0.6 to 1.5 cm. This compares to approximately 0.8 to 1.3 cm. for the 'BFP-420 Bright Red' cultivar.

*Branching pattern.*—Freely basal branching. No pinching is required to obtain self-branching. A vigorous self-branching growth habit is observed in the absence of a growth regulator.

*Petioles.*—Commonly approximately 3.3 to 4.1 cm. in length.

*Height.*—Approximately 18 to 22 cm. above a 10 cm. pot at 9 weeks under standard greenhouse condiitons. This compares to approximately 28 to 29 cm. for the 'BFP-420 Bright Red' cultivar.

I claim:

1. A new and distinct cultivar of Geranium plant named 'BFP-1328 Red', substantially as herein shown and described, which:

(a) exhibits attractive semi-double velvety intense red florets, (b) forms attractive medium green foliage with zonation, and (c) exhibits a vigorous self-branching growth habit in the absence of a growth regulator.

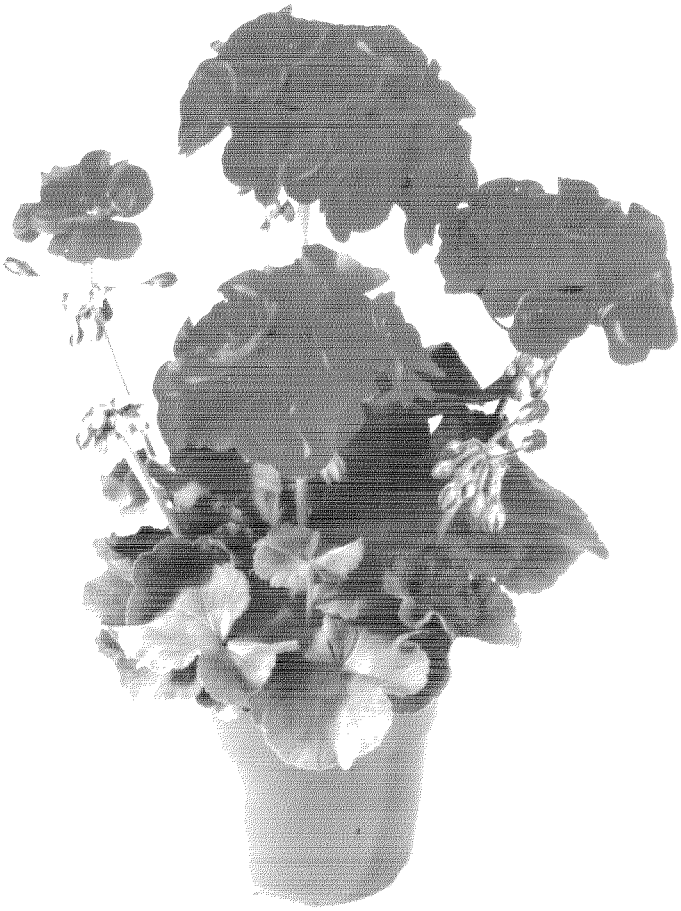

* * * * *